United States Patent
Kahler et al.

(10) Patent No.: US 8,241,235 B2
(45) Date of Patent: Aug. 14, 2012

(54) SURGICAL SWITCH MODE POWER SUPPLY AND SURGICAL DC POWER TOOL

(75) Inventors: Thomas Kahler, Seitingen-Oberflacht (DE); Roland Hoegerle, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 410 days.

(21) Appl. No.: 12/454,182

(22) Filed: May 12, 2009

(65) Prior Publication Data

US 2009/0292305 A1 Nov. 26, 2009

Related U.S. Application Data

(63) Continuation of application No. PCT/EP2007/062859, filed on Nov. 27, 2007.

(30) Foreign Application Priority Data

Dec. 7, 2006 (DE) .......................... 10 2006 058 867

(51) Int. Cl.
*A61B 18/04* (2006.01)
(52) U.S. Cl. ............................... 602/34; 602/32; 602/33
(58) Field of Classification Search .................. 363/144; 320/113, 114; 323/911; 606/32, 33, 34, 606/35, 39, 44, 79, 80, 81, 86 R, 167, 180, 606/41, 42
See application file for complete search history.

(56) References Cited

U.S. PATENT DOCUMENTS

| | | | |
|---|---|---|---|
| 4,835,410 A * | 5/1989 | Bhagwat et al. ................. 307/64 |
| 5,553,675 A * | 9/1996 | Pitzen et al. ................... 173/217 |
| 6,223,077 B1 | 4/2001 | Schweizer et al. |
| 6,296,065 B1 * | 10/2001 | Carrier ........................... 173/217 |
| 6,675,912 B2 * | 1/2004 | Carrier ........................... 173/217 |
| 6,773,438 B1 | 8/2004 | Knodel et al. |
| 6,960,894 B2 * | 11/2005 | Carusillo et al. ......... 318/400.01 |
| 7,176,656 B2 * | 2/2007 | Feldmann ...................... 320/114 |
| 7,259,975 B2 * | 8/2007 | Holme Pedersen et al. .. 363/146 |
| 7,303,556 B2 | 12/2007 | Metzger |
| 7,354,301 B2 | 4/2008 | Noguchi et al. |
| 7,403,399 B2 * | 7/2008 | Morbe et al. ................... 361/820 |
| 2002/0067080 A1 * | 6/2002 | Neumann ...................... 307/150 |
| 2003/0176856 A1 | 9/2003 | Howell |
| 2003/0220638 A1 | 11/2003 | Metzger |
| 2004/0054365 A1 * | 3/2004 | Goble ............................. 606/34 |

(Continued)

FOREIGN PATENT DOCUMENTS

DE 89 07 055 3/1990

(Continued)

*Primary Examiner* — Adolf Berhane
*Assistant Examiner* — Lakaisha Jackson
(74) *Attorney, Agent, or Firm* — Litspitz & McAllister, LLC

(57) ABSTRACT

In order to improve a surgical DC power tool such that it can be operated, where applicable, under sterile conditions, in particular, using conventional DC voltage supplies, a surgical switch mode power supply for a surgical DC power tool is provided. The switch mode power supply includes a switch mode power supply circuit arrangement, a switch mode power supply housing and a circuit receptacle formed in the housing of the switch mode power supply for accommodating the circuit arrangement of the switch mode power supply. The housing of the switch mode power supply has a switch mode power supply interface which is designed in such a manner that it can be brought into engagement with and/or connected to an interface of the DC power tool provided for a mains-independent energy source. Furthermore, an improved surgical DC power tool having such a power supply is provided.

36 Claims, 8 Drawing Sheets

U.S. PATENT DOCUMENTS

| | | | |
|---|---|---|---|
| 2004/0082944 A1 | 4/2004 | Howell | |
| 2005/0096661 A1* | 5/2005 | Farrow et al. | 606/79 |
| 2006/0189969 A1 | 8/2006 | Howell | |
| 2006/0238927 A1* | 10/2006 | Morbe et al. | 361/18 |
| 2009/0090763 A1* | 4/2009 | Zemlok et al. | 227/175.2 |
| 2009/0240245 A1* | 9/2009 | Deville et al. | 606/33 |
| 2009/0240246 A1* | 9/2009 | Deville et al. | 606/33 |

FOREIGN PATENT DOCUMENTS

| | | |
|---|---|---|
| DE | 103 17 531 | 11/2004 |
| DE | 10 2005 000 908 | 7/2006 |
| DE | 601 13 940 | 7/2006 |
| DE | 10 2005 015 654 | 10/2006 |
| EP | 0 754 437 | 1/1997 |
| EP | 1 322 245 | 7/2003 |
| EP | 1 469 583 | 10/2004 |
| JP | 03-503986 | 9/1991 |
| JP | 05-042162 | 2/1993 |
| WO | 89/07997 | 9/1989 |
| WO | 03/075442 | 9/2003 |
| WO | 03/079525 | 9/2003 |
| WO | 2005/112241 | 11/2005 |

* cited by examiner

SURGICAL SWITCH MODE POWER SUPPLY AND SURGICAL DC POWER TOOL

CROSS-REFERENCE TO RELATED APPLICATIONS

This application is a continuation of international application number PCT/EP2007/062859 filed on Nov. 27, 2007.

The present disclosure relates to the subject matter disclosed in international application number PCT/EP2007/062859 of Nov. 27, 2007 and German application number 10 2006 058 867.3 of Dec. 7, 2006, which are incorporated herein by reference in their entirety and for all purposes.

FIELD OF THE INVENTION

The present invention relates to a surgical switch mode power supply generally, and more specifically to a surgical switch mode power supply for a surgical DC power tool.

Furthermore, the present invention relates to a surgical DC power tool generally, and more specifically to a surgical DC power tool with a housing, a DC power consumer accommodated in the housing and an interface for a mains-independent energy source.

BACKGROUND OF THE INVENTION

Surgical DC power tools are used in surgery, for example, in the form of battery-driven or accumulator-driven surgical drive machines. Such drive machines, for example, drills or saws have the disadvantage that each battery or each accumulator can store only a limited amount of energy. During lengthy surgical procedures it is, therefore, possible for the battery to be emptied completely and to have to be charged again. The charging of the battery does, however, require time. Furthermore, a charger is required for the charging and/or a replacement battery in order to ensure the continued usability of the drive machine. In addition, it must be taken into account that the charging of the battery or any replacement thereof must take place under sterile conditions.

Therefore, it would be desirable to have a surgical switch mode power supply available for a surgical DC power tool and to have a surgical DC power tool such that it can, where applicable, be operated, in particular, under sterile conditions using conventional AC voltage supplies.

SUMMARY OF THE INVENTION

In a first aspect of the invention, a surgical switch mode power supply for a surgical DC power tool, comprises a switch mode power supply circuit arrangement, a switch mode power supply housing and a circuit receptacle formed in the housing of the switch mode power supply for accommodating the circuit arrangement of the switch mode power supply. The housing of the switch mode power supply has a switch mode power supply interface designed in such a manner that it is adapted to be brought into engagement with and/or connected to an interface of the DC power tool provided for a mains-independent energy source.

In a second aspect of the invention, a surgical DC power tool comprises a housing, a DC power consumer accommodated in the housing and an interface for a mains-independent energy source. A surgical switch mode power supply is provided which comprises a switch mode power supply circuit arrangement, a switch mode power supply housing and a circuit receptacle formed in the housing of the switch mode power supply for accommodating the circuit arrangement of the switch mode power supply. The housing of the switch mode power supply has a switch mode power supply interface designed in such a manner that it is adapted to be brought into engagement with the interface of the DC power tool provided for the mains-independent energy source

BRIEF DESCRIPTION OF THE DRAWINGS

The foregoing summary and the following description may be better understood in conjunction with the drawings figures, of which.

DETAILED DESCRIPTION OF THE INVENTION

Figure 1:
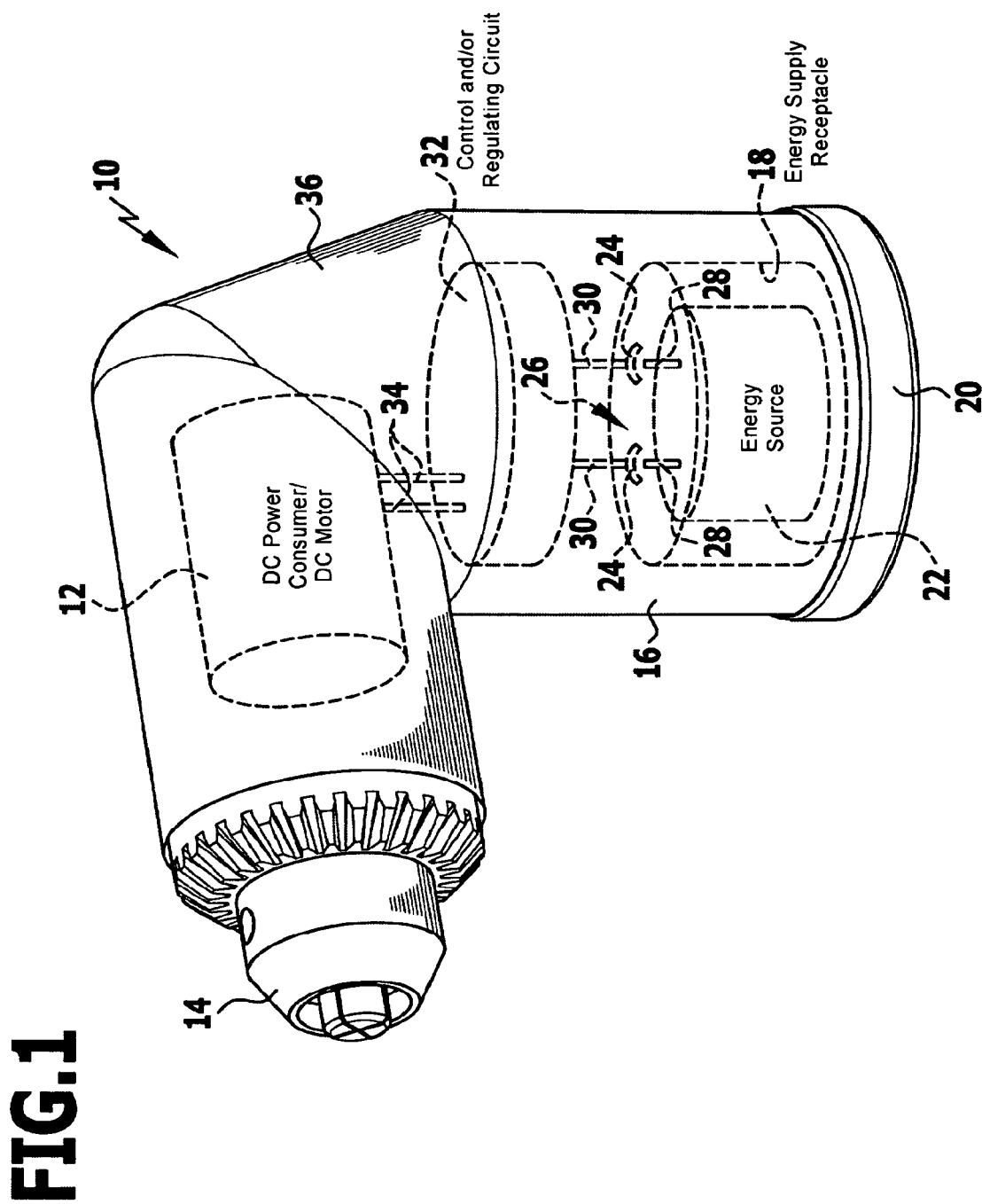
FIG. 1: shows a perspective schematic illustration of a surgical DC power tool with a mains-independent energy supply.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical switch mode power supply for a surgical DC power tool, comprising a switch mode power supply circuit arrangement, a switch mode power supply housing and a circuit receptacle formed in the housing of the switch-mode power supply for accommodating the circuit arrangement of the switch mode power supply, wherein the housing of the switch mode power supply has a switch mode power supply interface designed in such a manner that it is adapted to be brought into engagement with and/or connected to an interface of the DC power tool provided for a mains-independent energy source.

The surgical switch mode power supply according to the invention makes it possible to connect the surgical DC power tool, instead of to a battery, to an AC voltage or AC energy supply and thus supply it with energy. In particular, the surgical switch mode power supply can be designed in such a manner that it can be connected to the power supply system customary in a respective country, for example, the power supply system customary in Europe with an alternating voltage of 230 V and an alternating voltage frequency of between 50 and 60 Hz. Alternatively, it is, of course, also conceivable to use 110 V alternating voltage power supply systems with the switch mode power supply according to the invention for operating a surgical DC power tool. The surgical switch mode power supply has, in addition, the advantage that, particularly in the case of surgical procedures, for which a single battery charge is not sufficient, the surgical DC power tool required can be brought into engagement with the surgical switch mode power supply according to the invention and/or connected to it, whereby it can be operated for as long as required and a replacement of the energy supply is not required.

Furthermore, reference is made, in particular, to the fact that a surgical switch mode power supply within the meaning of the invention is not to be understood as a separate control device which can be connected to the surgical DC power tool via, for example, a cable connection. The surgical switch mode power supply is, on the contrary, intended to be brought into engagement with and/or connected directly to the DC power tool or to the interface for a mains-independent energy source.

It is advantageous when the interface of the switch mode power supply is designed in such a manner that it can be detachably connected to the interface of the DC power tool. In this case, it is possible to release the surgical switch mode power supply from the surgical DC power tool, for example, for the purpose of cleaning.

It is favorable when the interface of the switch mode power supply is designed in such a manner that it can be connected to the interface of the DC power supply electrically and/or mechanically. Particularly when the interface of the switch mode power supply is designed to correspond to the interface of the DC power tool, a battery or an accumulator, which can be used to supply energy to the DC tool, can be replaced by the surgical switch mode power supply temporarily or permanently in a simple manner.

Surgical DC power tools often have an energy supply receptacle for a battery which, in some cases, can also be closed. This makes it possible, in particular, to insert a non-sterilized battery into the energy supply receptacle, wherein sterility of the surgical DC power tool can still be ensured. In order to replace the mains-independent energy source in a simple manner, it is advantageous when the surgical switch mode power supply is designed in such a manner that it can be inserted at least partially into an energy supply receptacle of the DC power tool provided for a mains-independent energy source and can be fixed in or on it. This results altogether in a compact construction of the surgical DC power tool since the configuration of the surgical switch mode power supply, if at all, leads only to a slight increase in the size of the DC power tool.

The constructional size of the surgical DC power tool may be essentially retained when the housing of the switch mode power supply is designed in such a manner that it can be inserted into the energy supply receptacle of the DC power tool completely.

According to a preferred embodiment of the invention, it may be provided for the housing of the switch mode power supply to have a switch mode power supply housing opening, through which the circuit arrangement of the switch mode power supply can be inserted into the circuit receptacle and for the housing of the switch mode power supply to comprise a switch mode power supply housing cover for closing the housing opening of the switch mode power supply. Such a configuration makes it possible, in particular, to use a non-sterilized circuit arrangement of the switch mode power supply. This can be inserted into a sterilized housing of the switch mode power supply, for example, prior to its use, namely under sterile conditions so that the housing of the switch mode power supply, once it has been closed with the housing cover of the switch mode power supply, is completely sterile to the outside and thus all the requirements with regard to sterility not only of the switch mode power supply but also of the surgical DC power tool can be fulfilled.

The housing of the switch mode power supply can preferably be sterilized by steam. As a result, it can be processed, i.e., cleaned and steam sterilized, together with tools which can be operated by the surgical DC power tool. The production of the surgical switch mode power supply will be particularly inexpensive when the housing of the switch mode power supply is produced from at least one plastic material, preferably from a sterilizable plastic material. In addition, such a housing of the switch mode power supply can be sterilized completely safely and used in the sterile conditions required in an operating area.

In order to prevent germs from being able to exit from the circuit receptacle, it is favorable when at least one seal is provided for the fluid-tight sealing of the circuit receptacle.

The at least one seal is preferably arranged on the housing of the switch mode power supply so as to surround the housing opening of the switch mode power supply. In this way, sealing of the housing of the switch mode power supply relative to a surgical DC power tool is also possible even when no housing cover of the switch mode power supply for closing the housing opening of the switch mode power supply is provided. In this case, the seal seals the housing of the switch mode power supply directly relative to the surgical DC power tool, for example, relative to an energy supply receptacle thereof.

It is favorable when the at least one seal is arranged in such a manner that it seals the housing of the switch mode power supply and the housing cover of the switch mode power supply relative to one another when the housing cover of the switch mode power supply closes the housing opening of the switch mode power supply. With this configuration it is possible to equip the sterile housing of the switch mode power supply with a non-sterile circuit arrangement of the switch mode power supply, namely in such a manner that the housing of the switch mode power supply is still sterile after insertion of the circuit arrangement of the switch mode power supply. The closing and sealing of the housing opening of the switch mode power supply by means of the housing cover of the switch mode power supply serves to prevent germs from being able to exit from the housing of the switch mode power supply. The seal can be arranged on the housing cover of the switch mode power supply and/or on the housing of the switch mode power supply.

The at least one seal is favorably arranged in such a manner that it seals the housing of the switch mode power supply relative to a housing of a surgical DC power tool or an energy supply receptacle of the housing. As already explained, such a configuration enables the closure of the housing of the switch mode power supply with a housing cover of the switch mode power supply to be dispensed with. As a result, the construction of the surgical switch mode power supply is not only simplified but also more inexpensive.

In order to be able to connect the circuit arrangement of the switch mode power supply to the surgical DC power tool, it is favorable when first electrical contacts are provided on the housing of the switch mode power supply for connecting the circuit arrangement of the switch mode power supply to a DC power consumer of the surgical DC power tool. The first electrical contacts can, in particular, be arranged and designed in such a manner that they pass through the housing of the switch mode power supply in order to be able to connect the circuit arrangement of the switch mode power supply arranged in the circuit receptacle to the DC power consumer of the surgical DC power tool.

The first electrical contacts are preferably arranged on the housing cover of the switch mode power supply. As a result of the housing of the switch mode power supply being closed with the housing cover of the switch mode power supply, the first electrical contacts can be connected automatically to the circuit arrangement of the switch mode power supply during the closure of the housing of the switch mode power supply with the housing cover of the switch mode power supply.

According to a further, preferred embodiment of the invention, second electrical contacts can be provided on the housing of the switch mode power supply for the connection to third electrical contacts of a mains connection line or for the connection to fourth electrical contacts of a housing cover of the surgical DC power tool. With the second electrical contacts the switch mode power supply can be connected directly or indirectly to a mains connection line or a cable which allows a connection of the surgical switch mode power supply or of the surgical DC power tool to an alternating voltage or alternating current supply.

In order to simplify the construction of the switch mode power supply and minimize the number of free contacts, it is advantageous when a mains connection line is provided which is guided out of the housing of the switch mode power supply, is connected non-detachably to it and is connected electrically to the circuit arrangement of the switch mode power supply. For example, the mains connection line can have, in addition, a corresponding plug connector in order to connect the surgical switch mode power supply directly to a power supply system.

In order to make any dismantling of the surgical switch mode power supply prior to cleaning and sterilizing superfluous, it is favorable when the circuit arrangement of the switch mode power supply can be sterilized. The surgical switch mode power supply can then be sterilized as a whole. Any separation of the circuit arrangement of the switch mode power supply from the housing of the switch mode power supply is no longer necessary.

The circuit arrangement of the switch mode power supply is preferably cast into a sterilizable plastic material. As a result, the electronics of the circuit arrangement of the switch mode power supply, which are often sensitive to temperature and moisture, can be protected in order to make sterilization of the switch mode power supply possible, in particular, sterilization by steam.

The construction of the surgical switch mode power supply will be particularly simple when the plastic material is an epoxy resin.

The construction of the surgical switch mode power supply will be simplified even further when the circuit arrangement of the switch mode power supply and the housing of the switch mode power supply are connected non-detachably to one another. Moreover, any unintentional releasing of the circuit arrangement of the switch mode power supply from the housing of the switch mode power supply can be prevented in this way.

The circuit arrangement of the switch mode power supply is favorably surrounded by a moisture-repellant membrane. The membrane enables the circuit arrangement of the switch mode power supply to be used, in particular, in damp surroundings, as well. Even sterilization of the circuit arrangement of the switch mode power supply can be possible, depending on selection of the membrane.

It is advantageous when a DC consumer control and/or regulating circuit is provided which is surrounded at least partially by the housing of the switch mode power supply. This configuration has the advantage, in particular, that the surgical DC power tool itself need not be equipped with a DC consumer control and/or regulating circuit. This is then part of the surgical switch mode power supply and is connected automatically with it to the surgical DC power tool. The surgical DC power tool can, therefore, be equipped with other or improved control and/or regulating circuits in a simple manner without any additional dismantling of the DC power tool being necessary. In addition, a mains-independent energy supply of the surgical DC power tool, which comprises not only a battery but also a control and/or regulating circuit, can be replaced with such a surgical switch mode power supply.

The construction of the switch mode power supply will be particularly simple when the circuit arrangement of the switch mode power supply comprises the DC consumer control and/or regulating circuit. The DC consumer control and/or regulating circuit can, therefore, also be designed as part of the circuit arrangement of the switch mode power supply.

In order to insert, in particular, a non-sterilizable or non-sterile circuit arrangement of the switch mode power supply into a sterile housing of the switch mode power supply, it is advantageous when an insertion aid is provided for this purpose. The insertion aid ensures, in particular, that the non-sterile circuit arrangement of the switch mode power supply can come into contact with a part of the housing of the switch mode power supply or the surgical DC power tool which must remain absolutely sterile.

The construction of the insertion aid will be particularly simple when this is of a funnel-shaped design. For example, it can be designed in the form of a funnel-shaped, sterile film-type hose which can be connected to the DC power tool, in particular, its energy supply receptacle and through which the non-sterile circuit arrangement of the switch mode power supply can be inserted into the housing of the switch mode power supply or the energy supply receptacle of the DC power tool.

In order to be able to connect the surgical DC power tool to an available power supply system, it is advantageous when the circuit arrangement of the switch mode power supply comprises a rectifier circuit for converting an AC voltage into a DC voltage.

According to a preferred embodiment of the invention, it may be provided for the circuit arrangement of the switch mode power supply to have mains connection contacts for the direct or indirect connection to an AC voltage energy supply and DC connection contacts for the direct or indirect connection to a DC power tool or a DC consumer thereof. In principle, no additional components are, therefore, required to connect the surgical DC power tool to an available power supply system.

The construction of the switch mode power supply and connection thereof to a surgical DC power tool will be particularly simple when the first electrical contacts, the second electrical contacts, the third electrical contacts, the fourth electrical contacts, the mains connection contacts and/or the DC connection contacts are designed in the form of electrical plug connectors. The individual parts of the switch mode power supply can thus be pushed together in a simple manner, likewise the switch mode power supply for the connection to the surgical DC power tool.

Moreover, the present invention relates to a surgical DC power tool with a housing, a DC power consumer accommodated in the housing and an interface for a mains-independent energy source, wherein a surgical switch mode power supply is provided, said power supply comprising a switch mode power supply circuit arrangement, a switch mode power supply housing and a circuit receptacle formed in the housing of the switch mode power supply for accommodating the circuit arrangement of the switch mode power supply, and wherein the housing of the switch mode power supply has a switch mode power supply interface designed in such a manner that it is adapted to be brought into engagement with the interface of the DC power tool provided for the mains-independent energy source.

The DC power tool suggested in accordance with the invention makes it possible to use a surgical switch mode power supply, which makes an energy supply to the surgical DC power tool possible as a result of connection to an available power supply system, instead of a mains-independent energy supply.

In order, where applicable, to be able to replace the surgical switch mode power supply again by a mains-independent energy supply, it is advantageous when the interface of the switch mode power supply is designed in such a manner that it can be detachably connected to the interface of the DC power tool.

The interface of the switch mode power supply is preferably designed in such a manner that it can be connected to the interface of the DC power tool electrically and/or mechanically. Following connection of the surgical DC power tool to the switch mode power supply, the handling of the DC power tool for an operator does not, in practice, change in comparison with the use of a mains-independent energy supply in conjunction with the surgical DC power tool. Solely one electrical line for the connection of the switch mode power supply of the surgical DC power tool to the available power supply system is present, in addition.

In accordance with one preferred embodiment of the invention, it may be provided for the housing to have an energy supply receptacle for the mains-independent energy source and for the surgical switch mode power supply to be designed in such a manner that it can be inserted into the energy supply receptacle at least partially and be fixed in or on it. The energy supply receptacle can be equipped with a mains-independent energy source, for example, a battery or the surgical switch mode power supply, depending on the end purpose and use of the surgical DC power tool.

The handling of the surgical DC power tool does not, in practice, change for an operator when the surgical switch mode power supply is designed in such a manner that it can be inserted completely into the energy supply receptacle.

The interface is preferably arranged at or in the energy supply receptacle. This makes the handling of the surgical DC power tool easier, in particular, the replacement of a mains-independent energy supply by a surgical switch mode power supply.

In order to be able to use, in particular, a non-sterile surgical switch mode power supply in conjunction with the surgical DC power tool under sterile conditions, it is favorable when the DC power tool comprises a housing cover for closing the energy supply receptacle. The housing cover can preferably be sealed in a fluid-tight manner relative to the DC power tool.

The construction of the surgical DC tool will be particularly simple when at least one part of the housing of the switch mode power supply forms the housing cover. As a result, it is possible to connect the surgical switch mode power supply to the DC power tool, whereby the energy supply receptacle is closed by the housing of the switch mode power supply itself. An additional housing cover is not required.

Electrical connection contacts are preferably provided on the housing cover and these can be connected directly or indirectly to the surgical switch mode power supply on an inner side of the housing cover and to a mains connection line on an outer side of the cover. As a result, a mains connection line can be disconnected from the surgical DC power tool in a simple way and also connected to it again. Moreover, different mains connection lines with different plug adapters for different power supply systems can be connected to the surgical DC power tool in a simple way.

It is favorable when a mains connection line is provided for the detachable connection of the DC power tool to an AC voltage energy supply.

In accordance with one preferred embodiment of the invention, it may be provided for the surgical switch mode power supply to be one of the surgical switch mode power supplies described above.

In principle, it would be conceivable for the DC power consumer to be designed in the form of an electrical heater, or expressed more generally, in the form of a component without moveable parts. The DC power consumer is preferably a DC electric motor. A DC electric motor can serve the purpose, in particular, of forming a drill or milling machine or a saw.

It is advantageous when the surgical DC power tool is a surgical drill or a surgical saw. DC power tools of this type can be used in many different ways in conjunction with surgical procedures.

A DC power tool provided altogether with the reference numeral 10 is illustrated schematically in FIG. 1, namely by way of example in the form of a surgical drill. This comprises a DC power consumer 12 in the form of a DC motor. The DC motor can be designed, in particular, in the form of an electronically commutated DC motor. The DC consumer 12 serves to drive a drive shaft which is not illustrated and is coupled mechanically to a coupling 14 which serves for the connection to surgical tools, for example, drills or milling machines.

A gripping area 16 of the DC power tool 10 is equipped with an energy supply receptacle 18 in the form of a recess which can be closed with a housing cover 20, namely preferably fluid-tight. The energy supply receptacle 18 is designed in such a manner that it can accommodate a mains-independent energy source 22, for example, in the form of a battery or a rechargeable accumulator. Electrical contacts 24 provided in the energy supply receptacle 18 form an electrical interface 26. The interface 26 is designed and arranged in such a manner that the electrical contacts 24, when an energy source 22 is inserted, can be in contact and/or brought into engagement with connection contacts 28 thereof. The interface 26 is connected electrically via lines 30 to a control and/or regulating circuit 32 which is illustrated schematically in FIG. 1 and serves to control and/or regulate the DC power consumer 12. For this purpose, the control and/or regulating circuit 32 is connected electrically to the DC power consumer 12 via lines 34. Alternatively, the control and/or regulating circuit 32 can also be integrated into the energy source 22 and form with it a so-called energy and control unit. Only the DC power consumer 12 is then arranged in a housing 36 of the DC power tool in the case of such a configuration.

In the case where no mains-independent operation of the DC power tool 10 is desired, in particular, in cases where the capacity of the energy source 22 is not entirely adequate for a surgical procedure, the latter can also be replaced by a surgical switch mode power supply 38 according to the invention.

Figure 2:
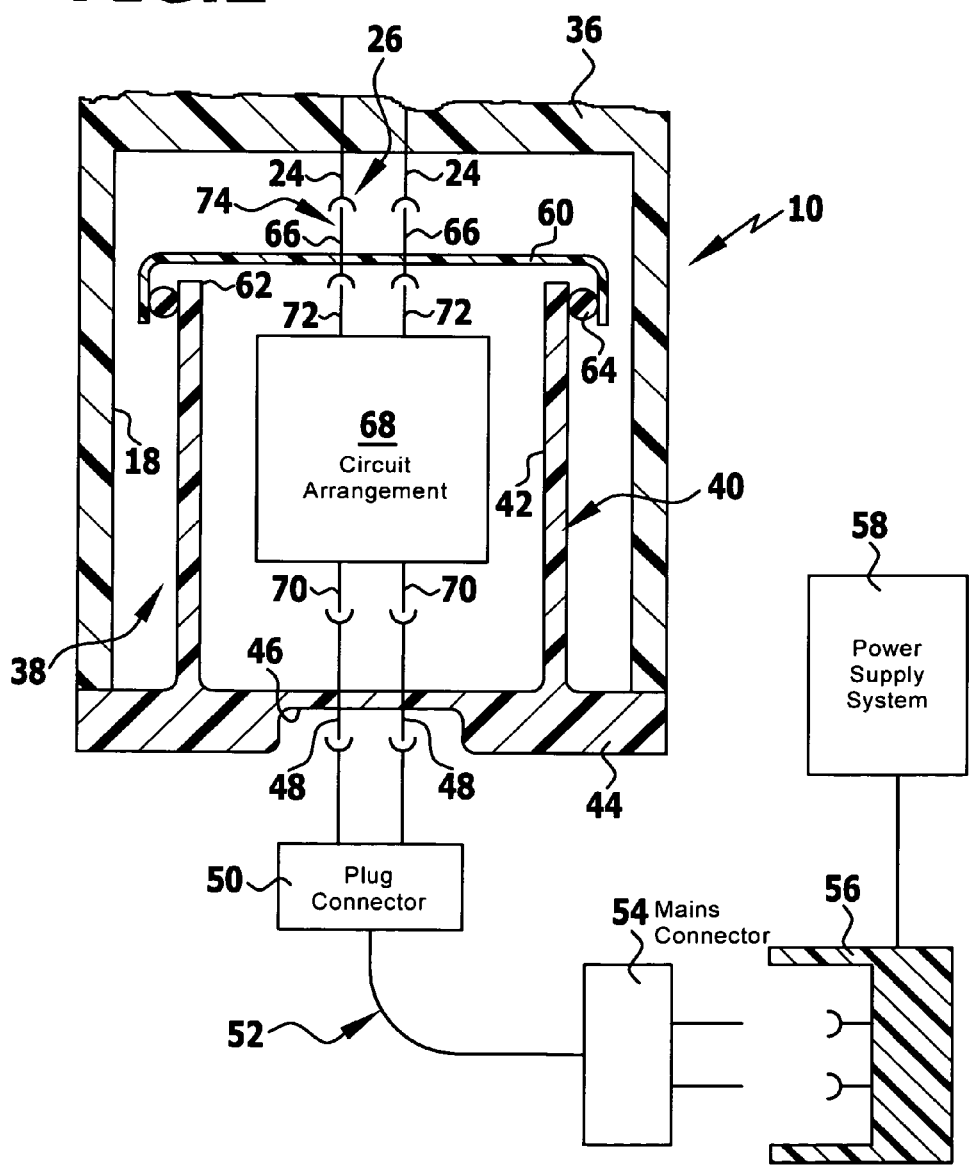
FIG. 2: shows a schematic illustration of a surgical DC power tool with a first embodiment of a surgical switch mode power supply.

A first embodiment of a switch mode power supply 38 is illustrated schematically in FIG. 2. It comprises an essentially sleeve-shaped housing 40 of the switch mode power supply which defines an essentially hollow cylindrical circuit receptacle 42. A base 44 of the housing 40 of the switch mode power supply is widened in a radial direction in a flange-like manner and thus forms at the same time a housing cover for closing the energy supply receptacle 18. A recess 46 with connection contacts 48 is provided on an outer side of the base 44, the contacts together forming a low-temperature connector socket and being connectable to a plug connector 50 of a mains connection cable 52 which, on the other hand, has at its other end a mains connector 54 which can be connected to a connector socket 56 connected to a power supply system 58.

The housing 40 of the switch mode power supply further comprises a housing cover 60 of the switch mode power supply for closing a housing opening 62 of the switch mode power supply. A seal 64 is arranged on the housing 40 of the switch mode power supply or on the housing cover 60 of the switch mode power supply so as to surround the housing opening 62 of the switch mode power supply in order to seal the circuit receptacle 42 tightly against germs. First electrical contacts 66 pass through the cover and form an interface of the switch mode power supply which can be in contact and/or brought into engagement with and/or connected to the interface 26 of the DC power tool 10. The first electrical contacts 66 pass through the housing cover 60 of the switch mode power supply. The connection contacts 48 pass through the base 44 of the housing 40 of the switch mode power supply.

A circuit arrangement 68 of the switch mode power supply can be inserted into the circuit receptacle 42 and comprises, in particular, a rectifier circuit for converting an alternating voltage into a direct voltage. Furthermore, it comprises mains connection contacts 70 which can be connected to the connection contacts 48 for the direct or indirect connection to an AC voltage energy supply, for example, the power supply system 58. Furthermore, DC connection contacts 72 are provided on the circuit arrangement 68 of the switch mode power supply and can be connected to the first electrical contacts 66 for the indirect connection to the interface 26 of the DC power tool 10.

The switch mode power supply 38 makes it possible to insert the circuit arrangement 68 of the switch mode power supply into the housing 40 of the switch mode power supply, which has previously been sterilized, via an insertion aid, for example, in the form of a sterile funnel which is not illustrated. Subsequently, the housing 40 of the switch mode power supply is closed tightly against germs with the housing cover 60 of the switch mode power supply. The switch mode power supply 38 can then be inserted into the energy supply receptacle 18 of the DC power tool 10 so that the interface 26 can be in contact and/or brought into engagement with a switch mode power supply interface 74 of the switch mode power supply 38 which comprises, in particular, the first electrical contacts 66. Optionally, the housing 40 of the switch mode power supply can, in particular, also be connected to the housing 36 mechanically, for example, by way of interlocking or screwing.

Figure 3:
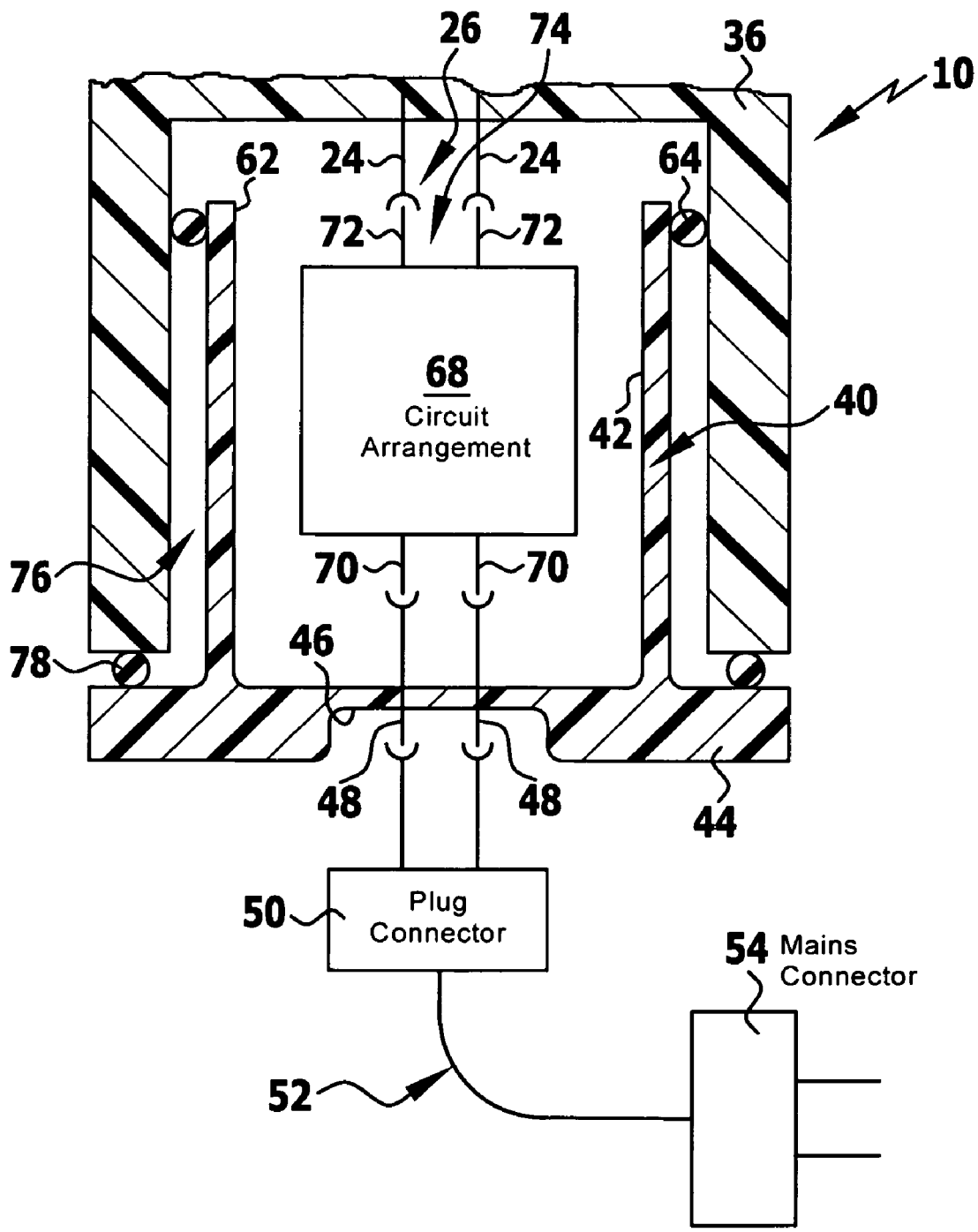
FIG. 3: shows a schematic illustration of a surgical DC power tool with a second embodiment of a surgical switch mode power supply.

A second embodiment of a surgical switch mode power supply is illustrated schematically in FIG. 3 and provided, altogether, with the reference numeral 76. The switch mode power supply 76 differs from the switch mode power supply 38 only in that the housing 40 of the switch mode power supply comprises no housing cover 60 for the switch mode power supply. The DC connection contacts 72 of the circuit arrangement 68 of the switch mode power supply therefore form, themselves, an interface 74 of the switch mode power supply which can be brought into engagement with the interface 26. The seal 64 is arranged on the housing 40 of the switch mode power supply so as to surround the housing opening 62 of the switch mode power supply. It serves the purpose of sealing the circuit receptacle 42 relative to the housing 36. Optionally, an additional seal 78 can be provided which seals the flange-like widened portion formed by the base 44, in addition, relative to the housing 36 of the DC power tool 10. The seal 78 can be held either on the base 44 or on the housing 36.

The switch mode power supply 76 also makes it possible to insert a non-sterile circuit arrangement 68 of the switch mode power supply into the housing 40 of the switch mode power supply, which has previously be sterilized, for example, via the sterile funnel mentioned above. Subsequently, the switch mode power supply 76 will be inserted into the energy supply receptacle 18 and sealed tightly against germs relative to the housing 36 by means of the seal 64 or, optionally, also with the seal 78.

Figure 4:
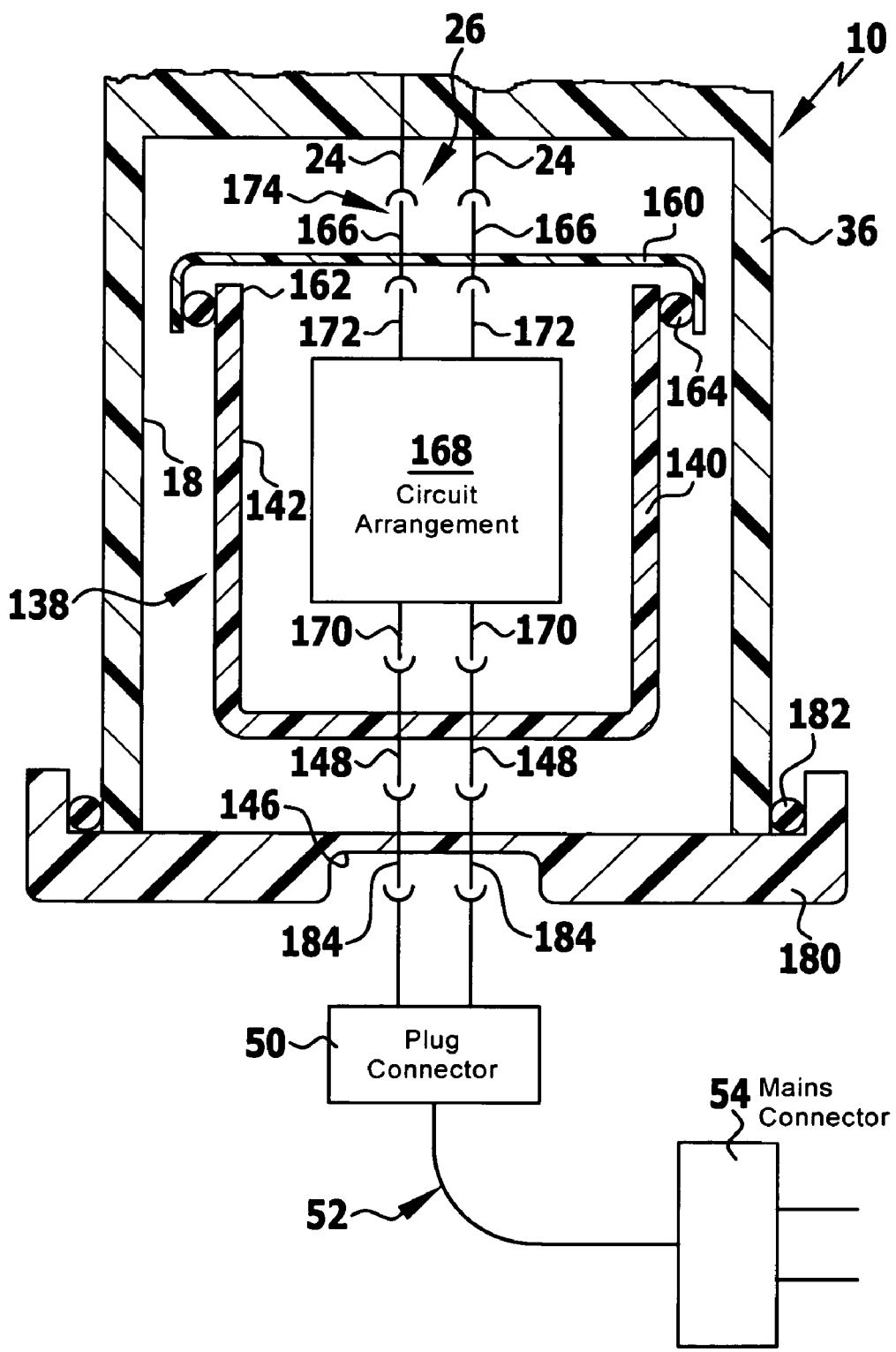
FIG. 4: shows a schematic illustration of a surgical DC power tool with a third embodiment of a surgical switch mode power supply.

A third embodiment of a switch mode power supply according to the invention is illustrated schematically in FIG. 4 and provided, altogether, with the reference numeral 138. It has a great similarity to the switch mode power supply 38 and so parts of the switch mode power supply 138 which correspond to parts of the switch mode power supply 38 are provided with reference numerals which have the same two end numbers. The essential difference to the switch mode power supply 38 described in conjunction with FIG. 2 is to be seen in the fact that a separate housing cover 180 is provided, with which the energy supply receptacle 18 can be closed. A fluid-tight/germ-tight sealing is achieved by a seal 182 which is arranged between the housing cover 180 and the housing 36 and is held either on the housing cover 180 or on the housing 36. A low-temperature connector socket is formed on the housing cover 180 by providing a recess 146 which points outwards and on which fourth electrical contacts 184 are arranged which pass, in addition, through the housing cover 180 and can be connected electrically to the connection contacts 148 projecting out of the housing 140 of the switch mode power supply. The mains connection cable 52 can, again, be connected to the low-temperature connector socket of the housing cover 180 in the manner described above. Mains connection contacts 170 illustrated in FIG. 4 corresponds to mains connection contacts 70 discussed above in connection with FIG. 2. DC connection contacts 172 illustrated in FIG. 4 corresponds to DC connection contacts 72 discussed above in connection with FIG. 2. Switch mode power supply interface 174 illustrated in FIG. 4 corresponds to switch mode power supply interface 74 discussed above in connection with FIG. 2.

The provision of a separate housing cover 180 has, in particular, the advantage that not only a non-sterile circuit arrangement 168 of the switch mode power supply can be used but also a non-sterile housing 140 of the switch mode power supply. The circuit arrangement 168 of the switch mode power supply can, consequently, be inserted first of all into the circuit receptacle 142. Subsequently, the housing opening 162 of the switch mode power supply can be closed with a housing cover 160 of the switch mode power supply. Optionally, the housing cover 160 of the switch mode power supply can also be dispensed with, however, and the DC connection contacts connected directly to the interface 26 instead of to the first electrical contacts 166. The switch mode power supply 138 prepared in this way can then be inserted into the energy supply receptacle 18 by means of, for example, an insertion aid described above and the receptacle can then be closed tightly against germs with the housing cover 180.

Figure 5:
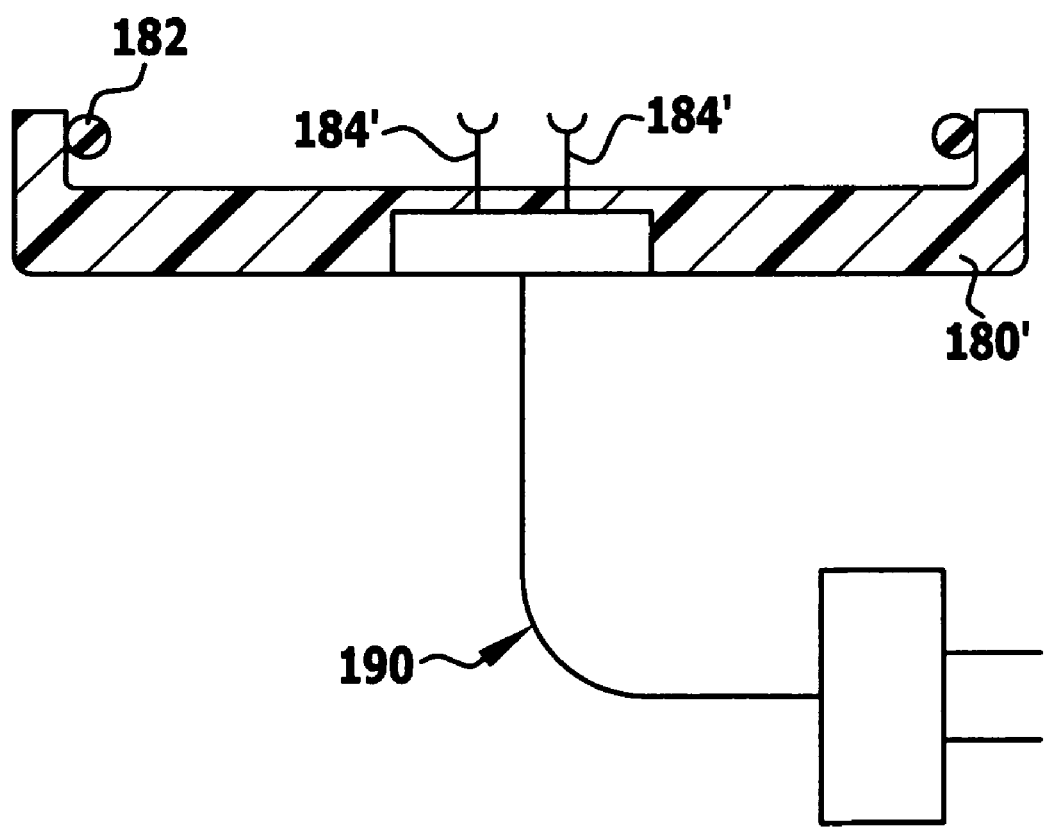
FIG. 5: shows a schematic illustration of an alternative embodiment of a housing cover for closing an energy supply receptacle of a surgical DC power tool.

Instead of a low-temperature connector socket, a mains connection cable 190 can be permanently connected to a housing cover 180'. In this case, a plug connector on the connection cable 190 for the connection to the low-temperature connector socket, which is not present, of the housing cover 180 can, in particular, be dispensed with. The mains connection cable 190 will, on the contrary, be connected directly to the fourth electrical contacts 184' which, on the other hand, can be connected to the connection contacts 148, for example, of the switch mode power supply 138. A schematic illustration of the housing cover 180' is shown in FIG. 5.

Figure 6:
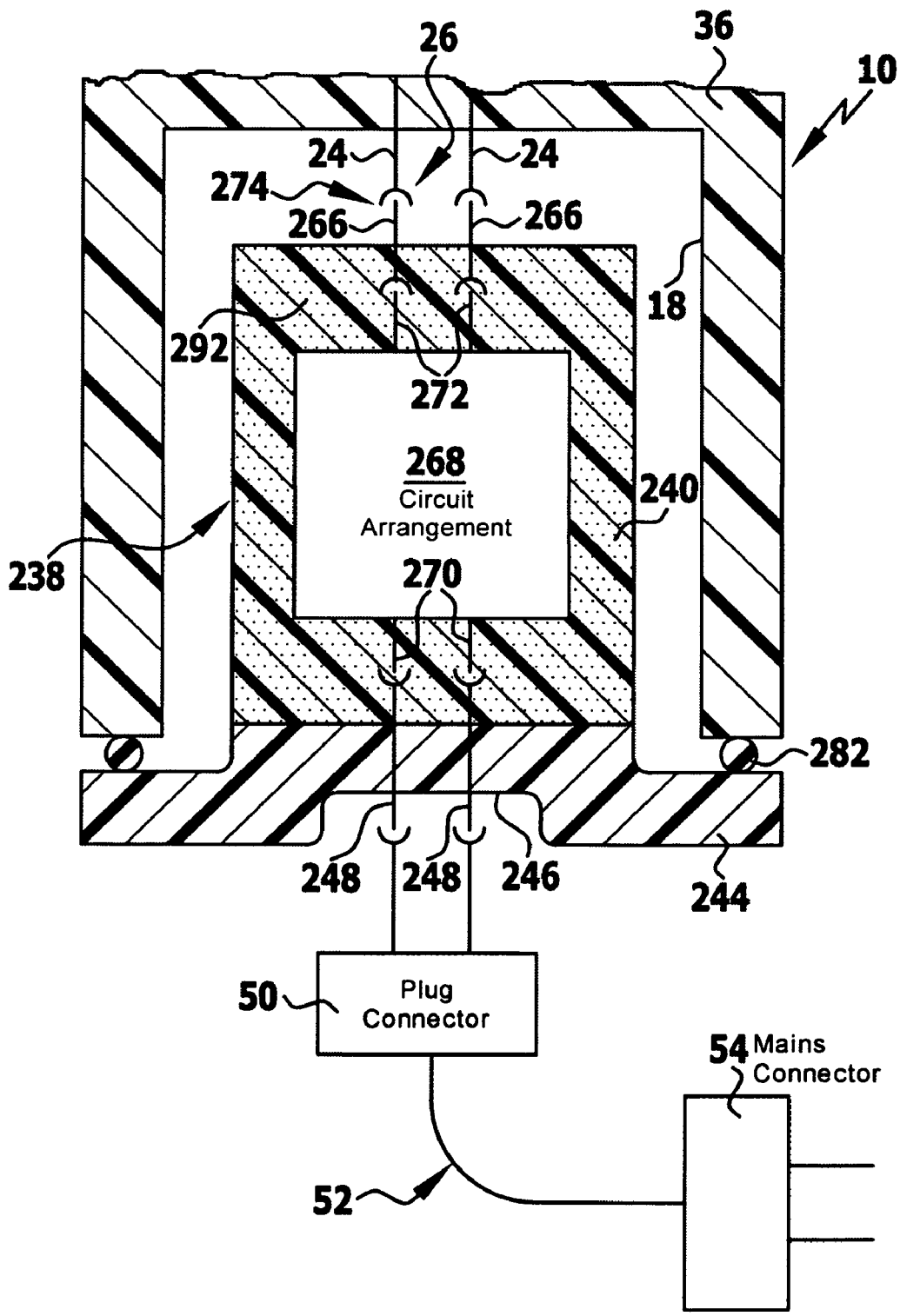
FIG. 6: shows a schematic illustration of a surgical DC power tool with a fourth embodiment of a surgical switch mode power supply.

A fourth embodiment of a surgical switch mode power supply is illustrated schematically in FIG. 6 and provided, altogether, with the reference numeral 238. It corresponds in its construction essentially to the switch mode power supply 38 but without a housing cover 60 for the switch mode power supply in the variation illustrated in FIG. 3. The circuit arrangement 268 of the switch mode power supply is built securely into the housing 240 of the switch mode power supply by, for example, vacuum casting with an epoxy resin 292. In this way, electronic components of the circuit arrangement 268 of the switch mode power supply, which are sensitive, in particular, to moisture and temperature, are protected and so the switch mode power supply 238 which forms a single unit can, itself, also be sterilized. Optionally, the casting can also form the housing of the switch mode power supply. A low-temperature connector socket provided on the base 244 of the housing 238 of the switch mode power supply can, on the other hand, be connected to a mains connection cable 52. The recess 246 illustrated in FIG. 6 corresponds to recesses 46 and 146 discussed above in connection with FIGS. 2 and 4, respectively. Connection contacts 248 illustrated in FIG. 6 corresponds to connection contacts 48 and 148 discussed above in connection with FIGS. 2 and 4, respectively. First electrical contacts 266 illustrated in FIG. 6 corresponds to first electrical contacts 66 and 166 discussed above in connection with FIGS. 2 and 4, respectively. Mains connection contacts 270 illustrated in FIG. 6 corresponds to mains connection contacts 70 discussed above in connection with FIG. 2. DC connection contacts 272 illustrated in FIG. 6 corresponds to DC connection contacts 72 discussed above in connection with FIG. 2. Switch mode power supply interface 274 illustrated in FIG. 6 corresponds to switch mode power supply interface 74 discussed above in connection with FIG. 2. Seal 282 illustrated in FIG. 6 corresponds to seal 182 discussed above in connection with FIG. 4.

Figure 7:
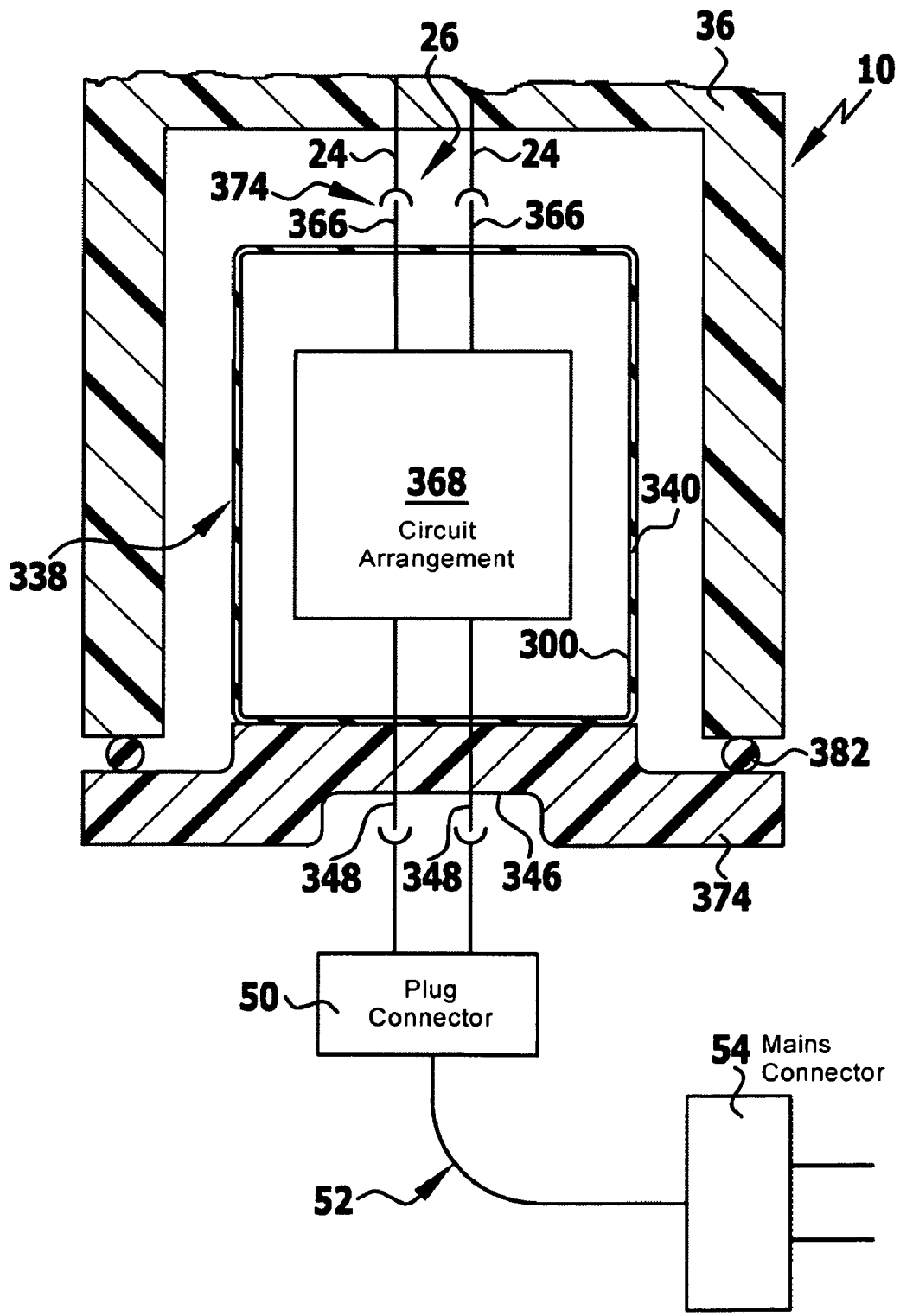
FIG. 7: shows a schematic illustration of a surgical DC power tool with a fifth embodiment of a surgical switch mode power supply.

In a fifth embodiment of a switch mode power supply 338, illustrated schematically in FIG. 7, a complete sterilizability thereof will be achieved in that the circuit arrangement 368 of the switch mode power supply is encased completely in a moisture-repellant membrane 300. The membrane 300 can be provided, for example, as an inner coating of the housing 340. As for the rest, the construction of the switch mode power supply 338 corresponds to the switch mode power supply 238. The recess 346 illustrated in FIG. 7 corresponds to recesses 46 and 146 discussed above in connection with FIGS. 2 and 4, respectively. Connection contacts 348 illustrated in FIG. 7 corresponds to connection contacts 48 and 148 discussed above in connection with FIGS. 2 and 4, respectively. First electrical contacts 366 illustrated in FIG. 7 corresponds to first electrical contacts 66 and 166 discussed above in connection with FIGS. 2 and 4, respectively. Switch mode power supply interface 374 illustrated in FIG. 7 corresponds to switch mode power supply interface 74 discussed above in connection with FIG. 2. Seal 382 illustrated in FIG. 7 corresponds to seal 182 discussed above in connection with FIG. 4.

Figure 8:
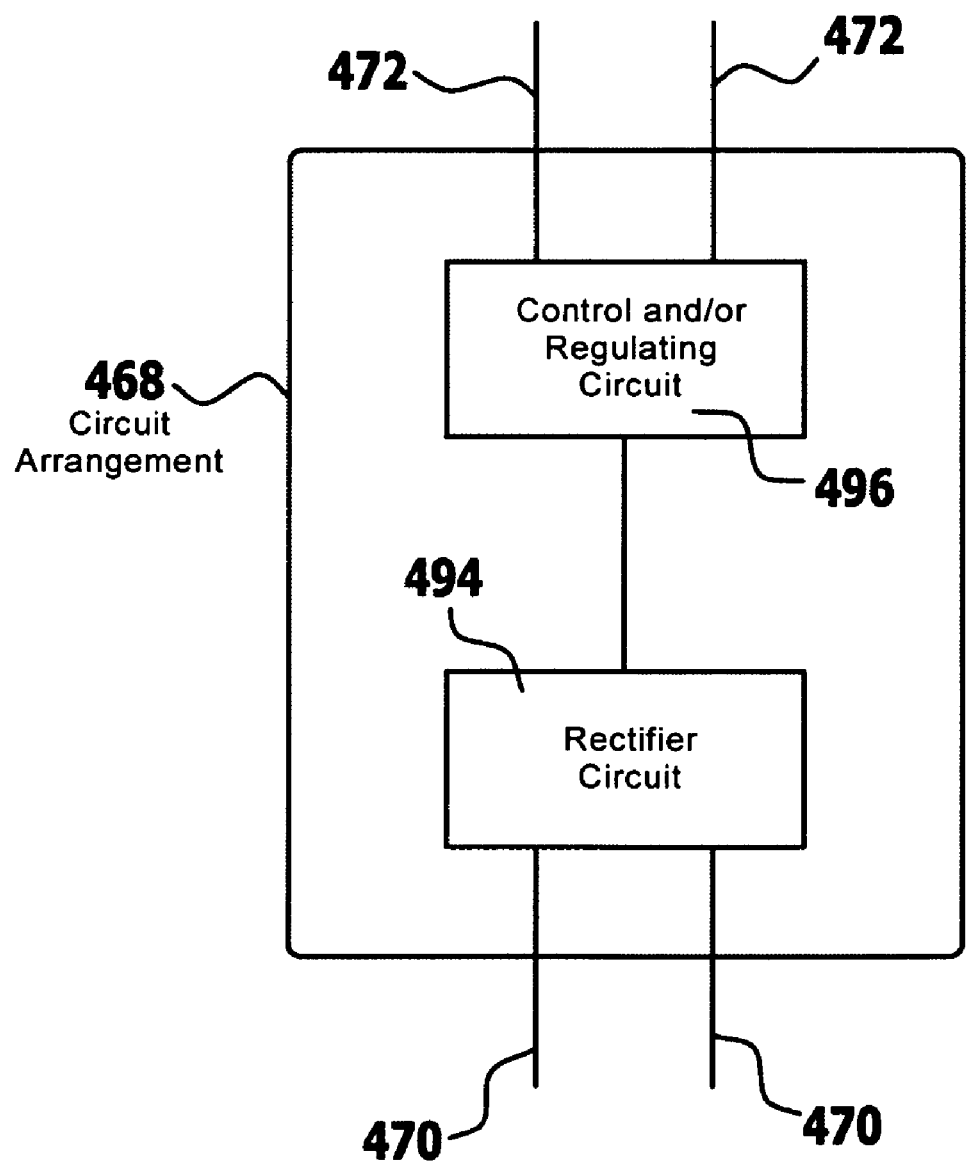
FIG. 8: shows a schematic illustration of an alternative embodiment of a circuit arrangement of the switch mode power supply.

If the DC power tool 10, as indicated in conjunction with the description of FIG. 1, has no control and/or regulating circuit 32 for the DC power consumer 12, such a control and/or regulating circuit 496 must be provided either at the mains-independent energy source 22 or at a switch mode power supply. In FIG. 8, a circuit arrangement 468 of the switch mode power supply is illustrated schematically and this has not only a rectifier circuit 494 but also a control and/or regulating circuit 496 for controlling and/or regulating the DC power consumer 12 of the DC power tool 10. Furthermore, the circuit arrangement 468 of the switch mode power supply has mains connection contacts 470 for the direct or indirect connection to an AC voltage energy supply and DC connection contacts 472 for the direct or indirect connection to the DC consumer 12 of the DC power tool 10.

The circuit arrangement 468 of the switch mode power supply can optionally replace the circuit arrangements 68, 168, 268 and 368 of the switch mode power supply.

Also in the case of the mains connection lines 52 described in conjunction with FIGS. 2, 3, 4, 6 and 7, mains connection lines can alternatively, as described in conjunction with FIG. 5, be non-detachably connected to a housing cover of the housing 36 or to the switch mode power supply housing of the respective switch mode power supply.

What is claimed is:

1. Surgical switch mode power supply for converting a surgical DC power tool to run on AC power, comprising:
   a switch mode power supply circuit arrangement adapted to be connected to an AC power source,
   a switch mode power supply housing,
   a circuit receptacle formed in the housing of the switch mode power supply for accommodating the circuit arrangement of the switch mode power supply, and
   a switch mode power supply interface disposed on the housing and adapted to directly abut and engage with an interface of the DC power tool which is provided for a mains-independent energy source,
   wherein the surgical switch mode power supply is adapted to be removably inserted into an energy supply receptacle of the DC power tool, the surgical switch mode power supply interface engaging with the interface of the DC power tool within the receptacle.

2. Surgical switch mode power supply as defined in claim 1, wherein the interface of the switch mode power supply is connectable to the interface of the DC power tool at least one of electrically and mechanically.

3. Surgical switch mode power supply as defined in claim 1, wherein the switch mode power supply is adapted to be inserted completely into the energy supply receptacle.

4. Surgical switch mode power supply as defined in claim 1, wherein:
   the housing of the switch mode power supply has a switch mode power supply housing opening,
   the circuit arrangement of the switch mode power supply being insertable through said opening into the circuit receptacle, and
   the housing of the switch mode power supply comprises a switch mode power supply housing cover for closing the housing opening of the switch mode power supply.

5. Surgical switch mode power supply as defined in claim 1, wherein the housing of the switch mode power supply is adapted to be sterilized by steam.

6. Surgical switch mode power supply as defined in claim 1, wherein the housing of the switch mode power supply is produced from at least one plastic material.

7. Surgical switch mode power supply as defined in claim 1, wherein at least one seal is provided for a fluid-tight sealing of the circuit receptacle.

8. Surgical switch mode power supply as defined in claim 7, wherein the at least one seal is arranged on the housing of the switch mode power supply so as to surround a housing opening of the switch mode power supply housing.

9. Surgical switch mode power supply as defined in claim 8, wherein the at least one seal is arranged in such a manner that it seals the housing of the switch mode power supply and a housing cover of the switch mode power supply relative to one another when the housing cover of the switch mode power supply closes the housing opening of the switch mode power supply.

10. Surgical switch mode power supply as defined in claim 7, wherein the at least one seal is arranged in such a manner that it seals the housing of the switch mode power supply relative to a housing of a surgical DC power tool or an energy supply receptacle of the housing.

11. Surgical switch mode power supply as defined in claim 1, wherein first electrical contacts are provided on the housing of the switch mode power supply for connecting the circuit arrangement of the switch mode power supply to a DC power consumer of the surgical DC power tool.

12. Surgical switch mode power supply as defined in claim 11, wherein the first electrical contacts are arranged on a housing cover of the switch mode power supply.

13. Surgical switch mode power supply as defined in claim 1, wherein second electrical contacts are provided on the housing of the switch mode power supply for the connection to third electrical contacts of a mains connection line or for the connection to fourth electrical contacts of a housing cover of the surgical DC power tool.

14. Surgical switch mode power supply as defined in claim 13, wherein at least one of the first electrical contacts, the second electrical contacts, the third electrical contacts, the fourth electrical contacts, mains connection contacts for the direct or indirect connection to an AC voltage energy supply and DC connection contacts for the direct or indirect connection to a DC power tool or a DC consumer comprise electrical plug connectors.

15. Surgical switch mode power supply as defined in claim 1, wherein:
a mains connection line is provided,
said connection line is guided out of the housing of the switch mode power supply and is connected non-detachably to the housing, and
the connection line is connected electrically to the circuit arrangement of the switch mode power supply.

16. Surgical switch mode power supply as defined in claim 1, wherein the circuit arrangement of the switch mode power supply is adapted to be sterilized.

17. Surgical switch mode power supply as defined in claim 1, wherein the circuit arrangement of the switch mode power supply is cast into a sterilizable plastic material.

18. Surgical switch mode power supply as defined in claim 17, wherein the plastic material is an epoxy resin.

19. Surgical switch mode power supply as defined in claim 1, wherein the circuit arrangement of the switch mode power supply and the housing of the switch mode power supply are connected non-detachably to one another.

20. Surgical switch mode power supply as defined in claim 1, wherein the circuit arrangement of the switch mode power supply is surrounded by a moisture-repellant membrane.

21. Surgical switch mode power supply as defined in claim 1, wherein a DC consumer control and/or regulating circuit is provided, said circuit being surrounded at least partially by the housing of the switch mode power supply.

22. Surgical switch mode power supply as defined in claim 21, wherein the circuit arrangement of the switch mode power supply comprises the DC consumer control and/or regulating circuit.

23. Surgical switch mode power supply as defined in claim 1, wherein an insertion aid is provided for insertion of the circuit arrangement of the switch mode power supply into the housing of the switch mode power supply.

24. Surgical switch mode power supply as defined in claim 23, wherein the insertion aid is of a funnel-shaped design.

25. Surgical switch mode power supply as defined in claim 1, wherein the circuit arrangement of the switch mode power supply comprises a rectifier circuit for converting an AC voltage into a DC voltage.

26. Surgical switch mode power supply as defined in claim 1, wherein the circuit arrangement of the switch mode power supply has mains connection contacts for direct or indirect connection to an AC voltage energy supply and DC connection contacts for direct or indirect connection to the DC power tool or a DC consumer thereof.

27. Surgical DC power tool comprising:
a housing,
a DC power consumer accommodated in the housing,
an interface for a mains-independent energy source,
a surgical switch mode power supply for converting the surgical DC power tool to run on AC power, said power supply comprising:
a switch mode power supply circuit arrangement adapted to be connected to an AC power source,
a switch mode power supply housing,
a circuit receptacle formed in the housing of the switch mode power supply for accommodating the circuit arrangement of the switch mode power supply, and
a switch mode power supply interface disposed on the switch mode power supply housing adapted to directly abut and engage with the interface of the DC power tool provided for the mains-independent energy source,
wherein the surgical switch mode power supply is adapted to be removably inserted into an energy supply receptacle of the DC power tool, the surgical switch mode power supply interface engaging with the interface of the DC power tool within the receptacle.

28. Surgical DC power tool as defined in claim 27, wherein the interface of the switch mode power supply is connectable to the interface of the DC power tool at least one of electrically and mechanically.

29. Surgical DC power tool as defined in claim 27, wherein the surgical switch mode power supply is insertable completely into the energy supply receptacle.

30. Surgical DC power tool as defined in claim 27, wherein the interface of the surgical switch mode power supply is arranged at or in the energy supply receptacle.

31. Surgical DC power tool as defined in claim 27, wherein the DC power tool comprises a housing cover for closing the energy supply receptacle.

32. Surgical DC power tool as defined in claim 31, wherein at least one part of the housing of the switch mode power supply forms the housing cover.

33. Surgical DC power tool as defined in claim 31, wherein electrical connection contacts are provided on the housing cover, said contacts being connectable directly or indirectly to the surgical switch mode power supply on an inner side of the housing cover and to a mains connection line on an outer side of the cover.

34. Surgical DC power tool as defined in claim 27, wherein a mains connection line is provided for a detachable connection of the DC power tool to an AC voltage energy supply.

35. Surgical DC power tool as defined in claim 27, wherein the DC power consumer is a DC electric motor.

36. Surgical DC power tool as defined in claim 27, wherein the surgical DC power tool is a surgical drill or a surgical saw.

* * * * *